(12) United States Patent
Lintner

(10) Patent No.: US 7,156,864 B2
(45) Date of Patent: Jan. 2, 2007

(54) SUTURE ANCHOR

(76) Inventor: David Lintner, 6348 Mercer St., Houston, TX (US) 77005

( * ) Notice: Subject to any disclaimer, the term of this patent is extended or adjusted under 35 U.S.C. 154(b) by 0 days.

(21) Appl. No.: 10/109,032

(22) Filed: Mar. 28, 2002

(65) Prior Publication Data

US 2003/0187477 A1 Oct. 2, 2003

(51) Int. Cl.
*A61B 17/04* (2006.01)
(52) U.S. Cl. .......................... 606/232; 606/53
(58) Field of Classification Search ............ 606/53, 606/60, 65, 72, 73, 232, 233
See application file for complete search history.

(56) References Cited

U.S. PATENT DOCUMENTS

| 4,870,957 | A | * | 10/1989 | Goble et al. ............... 606/73 |
| 5,980,558 | A | * | 11/1999 | Wiley ....................... 606/232 |
| 6,027,523 | A | * | 2/2000 | Schmieding ............... 606/232 |

* cited by examiner

*Primary Examiner*—Glenn K. Dawson
(74) *Attorney, Agent, or Firm*—Duane Morris LLP

(57) ABSTRACT

The present invention relates to a threaded suture anchor for use in securing tissue to bone. The present invention further relates to the combination of a suture anchor and a suture without the need to tie a knot in the suture.

19 Claims, 2 Drawing Sheets

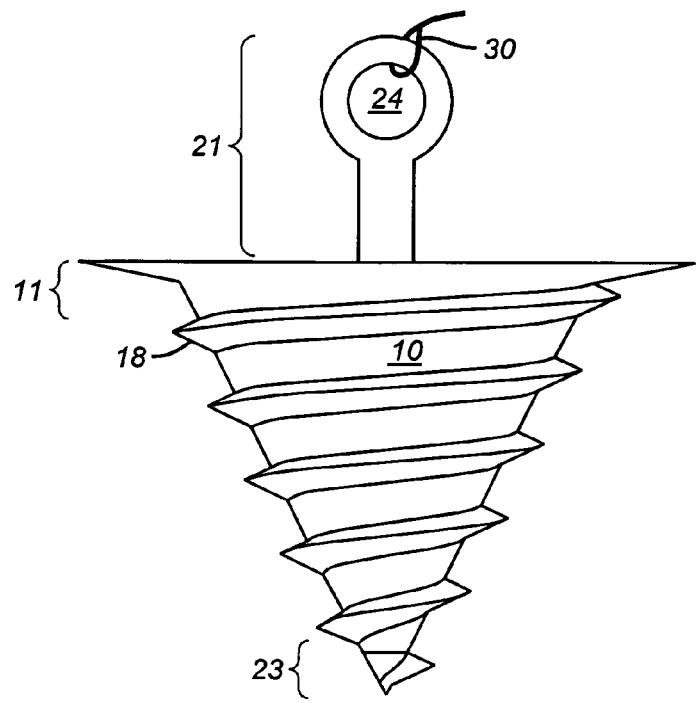
FIG. 2
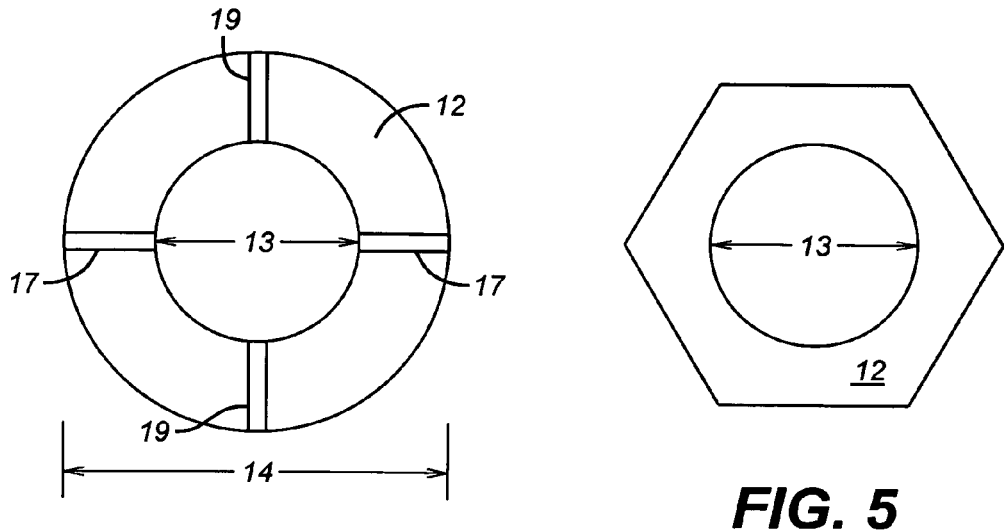
FIG. 3
FIG. 5

SUTURE ANCHOR

BACKGROUND OF THE INVENTION

1. Field of the Invention

The present invention relates to a threaded suture anchor for use in securing tissue to bone. The present invention further relates to the combination of a suture anchor and a suture without the need to tie a knot in the suture.

2. Description of the Prior Art

Prior art suture anchors used in orthopedic surgery fall into two different categories. The first category is screw in suture anchors. The second category is suture anchors which are hammered into the bone. Prior art screw in suture anchors require a surgeon to tie knots in the suture. Such knot tying often requires arthroscopic techniques. It is often extremely difficult and time consuming to tie a secure knot using arthroscopic techniques.

The other category of suture anchors are hammered into a hole that is predrilled into the bone. The suture anchors are impacted or hammered into the glenoid. One of these "hammered in" suture anchors is a knotless anchor. The term "knotless anchors," as used herein, refers to a suture anchor that can be securely affixed to a suture and the suture affixed to tissue without tying a knot in the suture.

The present invention eliminates the need to tie knots in the suture and takes advantage of the superior fixation strength inherent in a screw in type of suture anchor. The present invention is thus easier to use and appropriate for use in the humeral head or other areas of cancellous bone.

SUMMARY OF THE INVENTION

The present invention is directed toward a suture anchor. The suture anchor comprises an outer conical member comprising a first end region comprising a top annular surface having an inner diameter and an outer diameter. The outer conical member further comprises a second end region opposite the first end region, screw like threads mounted on the conical member and a central channel extending longitudinally through the entire length of the conical member. The diameter of the first end region is greater than the diameter of the second region of the outer conical member.

The invention further comprises an anchoring member rotatably affixed in the central channel. The anchoring member has an upper end region extending out of the channel. The upper end region comprises a suture securing receptacle. The anchoring member further comprises a lower end region opposite the upper end region and extending beyond the second end region of said outer conical member. Multiple suture anchors of the design of the present invention may be employed to secure tissue to bone.

DESCRIPTION OF THE DRAWINGS

FIG. 2 is a side view of a second embodiment of the present invention.

FIG. 3 is top view of a first embodiment of the present invention.

FIG. 5 is a top view of a second embodiment of the invention, comprising a hexagonal head.

DESCRIPTION OF THE PREFERRED EMBODIMENTS

Figure 1:
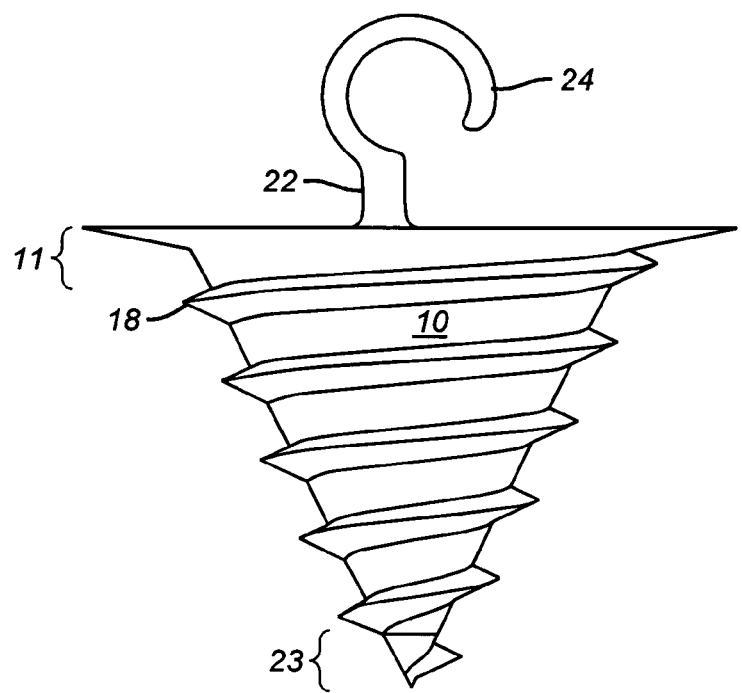
FIG. 1 is a side view of a first embodiment of the present invention.

The present invention is directed toward a suture anchor. The suture anchor of the present invention comprises an outer conical member 10 comprising a first end region 11 comprising a top annular surface 12 having an inner diameter 13 and an outer diameter 14, as shown in FIGS. 1 and 3. In a preferred embodiment, the top annular surface comprises a first groove 17 extending across the diameter of the top annular surface, as shown in FIG. 3. In another preferred embodiment, the top surface comprises the second groove 19 extending across the diameter of the top annular surface and oriented perpendicular to the first groove, as shown in FIG. 3.

In other embodiments, the top surface can be shaped and sized to mate with a wrench. Applicable shapes include a square and a hexagon. An open end or box end wrench can be used to apply torque to the outer conical member in order to screw it into or out of a bone.

Figure 4:
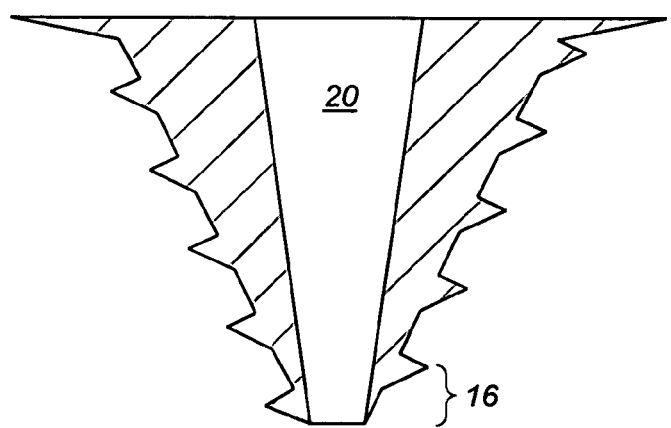
FIG. 4 is cross sectional view of the outer conical member of the present invention.

The outer conical member further comprises a second end region 16 opposite the first end region, as shown in FIG. 4. Screw like threads 18 are mounted on the conical member, as shown in FIG. 1. The outer conical member further comprises a central channel 20 extended longitudinally through the entire length of the conical member, as shown in FIG. 4. In a preferred embodiment, the threads are large enough to purchase cancellous bone. In a preferred embodiment, these threads have a spread of 5–6 millimeters.

The invention further comprises an anchoring member 22 rotatably attached in the central channel. This rotational affixation allows the anchoring member to rotate freely, thereby permitting the outer conical member to be advanced into the bone without twisting a suture attached to the anchoring member. The anchoring member has an upper end region 21 extending out of the channel, as shown in FIG. 2.

The upper end region has a suture securing receptacle 24. In one preferred embodiment, the suture securing receptacle is a hook, as shown in FIG. 1. In a preferred embodiment, the hook has a diameter that is less than the outer diameter of the top annular surface, as shown in FIG. 1. In another preferred embodiment, the suture securing receptacle is an eyelet, as shown in FIG. 2. In a preferred embodiment, a suture is manufactured as a closed loop affixed to the suture securing receptacle.

The anchoring member further has a lower end region 23 opposite the first end region and extending beyond the second end region of said outer conical member.

The foregoing disclosure and description of the invention are illustrative and explanatory. Various changes in the size, shape, and materials, as well as in the details of the illustrative construction may be made without departing from the spirit of the invention.

What is claimed is:

1. A suture anchor comprising:
   a. an outer conical member comprising a first end region comprising a top annular surface having an inner diameter and an outer diameter, a second end region opposite said first end region, threads mounted on said conical member, and a central channel extending longitudinally through the entire length of said conical member; and
   b. an anchoring member rotatably attached in said central channel, said anchoring member having an upper end region extending out of said channel, said upper end region comprising a suture securing receptacle, and said anchoring member having a pointed lower end region opposite said upper end region and extending beyond the second end region of said outer conical member.

2. The suture anchor of claim 1, wherein said suture securing receptacle is a hook.

3. The suture anchor of claim 2, wherein said hook has a diameter that is less than the outer diameter of said top annular surface.

4. The suture anchor of claim 2 further comprising a suture loop attached to said hook.

5. The suture anchor of claim 1, wherein said suture securing receptacle is an eyelet.

6. The suture anchor of claim 5, further comprising a suture loop extending through said eyelet.

7. The suture anchor of claim 1, wherein said top annular surface is hexagonal.

8. The suture anchor of claim 1, wherein said top annular surface comprises a first groove extending across the diameter of said top annular surface.

9. The suture anchor of claim 8, further comprising a second groove extending across the diameter of said top annular surface and oriented perpendicular to said first groove.

10. The suture anchor of claim 1, wherein said threads are large enough to purchase cancellous bone.

11. The suture anchor of claim 1, wherein threads are mounted on said lower end region.

12. A suture anchor comprising:
  a. an outer conical member comprising a first end region comprising a top annular surface having an inner diameter and an outer diameter, a second end region opposite said first end region, threads mounted on said conical member, and a central channel extending longitudinally through the entire length of said conical member;
  b. an anchoring member rotatably attached in said central channel, said anchoring member having an upper end region extending out of said channel, said upper end region comprising a suture securing receptacle, and said anchoring member having a pointed lower end region opposite said upper end region and extending beyond the second end region of said outer conical member; and
  c. a suture loop attached to said suture securing receptacle.

13. The suture anchor of claim 12, wherein said suture securing receptacle is an eyelet.

14. The suture anchor of claim 13, wherein said top annular surface is hexagonal.

15. The suture anchor of claim 14, wherein said top annular surface comprises a first groove extending across the diameter of said top annular surface.

16. The suture anchor of claim 15, wherein said threads are large enough to purchase cancellous bone.

17. The suture anchor of claim 12, wherein threads are mounted on said lower end region.

18. A suture anchor comprising:
  a. an outer conical member comprising a first end region comprising a top annular surface having an inner diameter and an outer diameter, a second end region opposite said first end region, threads mounted on said conical member, and a central channel extending longitudinally through the entire length of said conical member; and
  b. an anchoring member rotatably mounted in said central channel, said anchoring member having an upper end region comprising a suture securing receptacle, and said anchoring member having a pointed lower end region opposite said upper end region and extending beyond the second end region of said outer conical member.

19. The suture anchor of claim 18, wherein said top annular surface comprises a first groove extending across the diameter of said top annular surface.

* * * * *